United States Patent [19]

Runge et al.

[11] Patent Number: 4,968,422
[45] Date of Patent: Nov. 6, 1990

[54] PULSATILE FLOW HEMODIALYSIS

[76] Inventors: Thomas M. Runge, 2501 Galewood Pl., Austin, Tex. 78703; Michael R. Sheller, 4611 Avenue M, Austin, Tex. 78751

[21] Appl. No.: 156,809

[22] Filed: Feb. 17, 1988

Related U.S. Application Data

[63] Continuation of Ser. No. 877,748, Jun. 23, 1986, abandoned.

[51] Int. Cl.$^5$ .............................................. B01D 61/28
[52] U.S. Cl. ......................... 210/321.69; 210/321.72; 210/416.1
[58] Field of Search ............. 604/4.5; 210/356, 416.1, 210/637, 646, 106, 195.2, 321.65, 321.69, 321.72, 321.73, 321.74, 321.75, 321.76, 321.77, 321.78, 321.79, 321.8, 321.81

[56] References Cited

U.S. PATENT DOCUMENTS

| | | | |
|---|---|---|---|
| 3,989,626 | 11/1976 | Bentley et al. | 210/321.81 |
| 4,004,299 | 1/1977 | Runge | 623/3 |
| 4,058,855 | 11/1977 | Runge | 623/3 |
| 4,075,091 | 2/1978 | Bellhouse | 210/637 |
| 4,143,425 | 3/1979 | Runge | 623/3 |
| 4,293,961 | 10/1981 | Runge | 623/3 |
| 4,357,239 | 11/1982 | Bellhouse et al. | 210/356 X |
| 4,370,983 | 2/1983 | Lichtenstein | 210/321.65 |
| 4,492,531 | 1/1985 | Kenji et al. | 210/321.65 |
| 4,662,829 | 5/1987 | Nehring | 604/153 |

*Primary Examiner*—W. Gary Jones
*Attorney, Agent, or Firm*—Brady, O'Boyle & Gates

[57] ABSTRACT

The use of a pulsatile flow blood pump in a hemodialysis system is disclosed. In comparison to the customary steady flow blood pump of the prior art, the pulsatile flow blood pump clears urea, a low molecular weight molecule, from the bood approximately three times as fast as does the steady flow roller pump commonly used on a worldwide basis for hemodialysis. Large molecules, such as vitamin $B_{12}$ are also cleared more rapidly by the pulsatile flow pump, but less rapidly than the smaller molecules. Total time of dialysis is reduced and the results obtained by using the pulsatile flow blood pump are more physiologic, in that the more harmful molecules, urea, are selectively cleared more rapidly while the larger more desirable molecules, vitamin $B_{12}$, are retained.

1 Claim, 1 Drawing Sheet

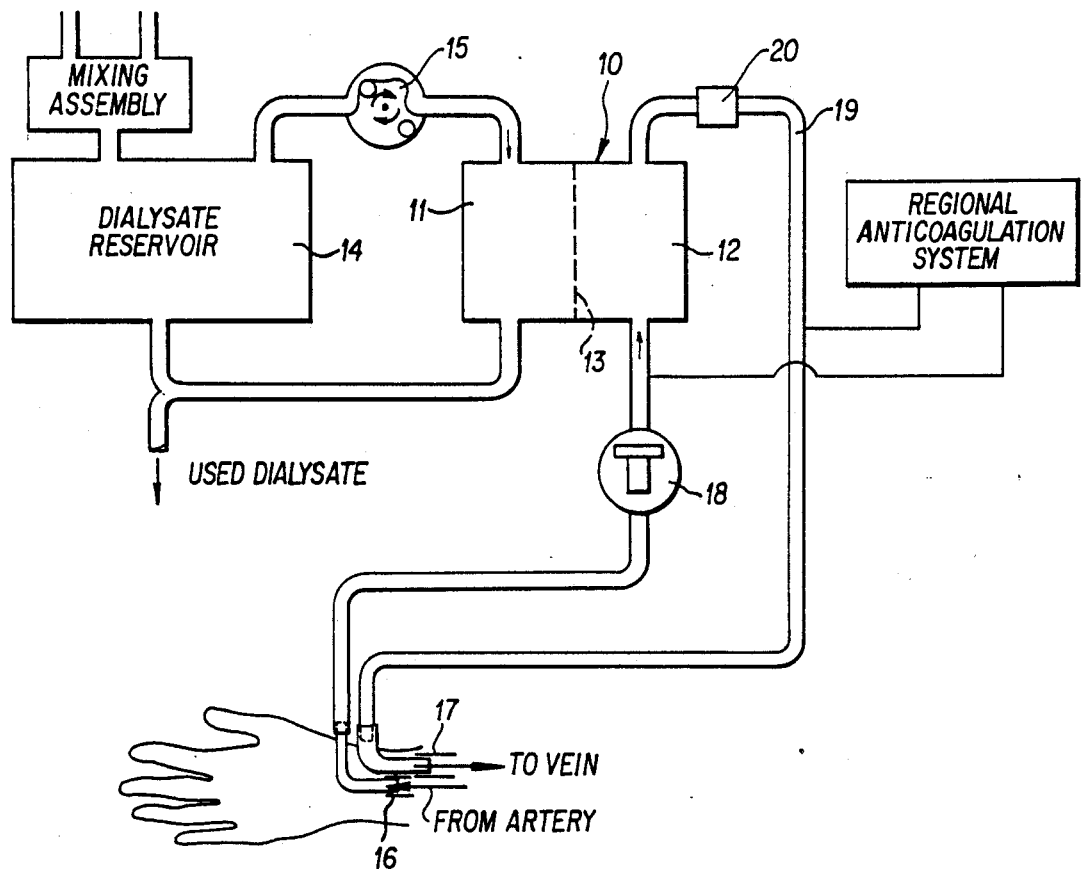

PULSATILE FLOW HEMODIALYSIS

This is a continuation of application Ser. No. 06/877,748 filed June 23, 1986 now abandoned.

BACKGROUND OF THE INVENTION

1. Technical Field:

The present invention relates broadly to an improved hemodialysis system, and more particularly relates to a hemodialysis system utilizing a pulsatile flow blood pump.

2. Description of the Prior Art:

Commonly, in the prior art pertaining to hemodialysis, steady flow pumps typified by a Sarns 3500 Roller Pump are used to pump the dialysate and the blood in the system.

Also known in the prior art are pulsatile flow blood pumps used for cardiac assistance and replacement and in cardio-pulmonary bypass devices. Examples of the prior art pulsatile flow pumps are disclosed in U.S. Pat. Nos. 4,004,299; 4,058,855; 4,143,425; and 4,293,961, issued to Thomas M. Runge.

The objective of this invention is to significantly improve the efficiency of the hemodialysis process by eliminating the prior art steady flow blood pump and replacing it with a pulsatile flow pump, whereby hemodialysis is caused to more closely simulate the natural blood purification process performed by kidneys in conjunction with the pulsatile flow pumping action of the heart. Laboratory test results indicate that by using a pulsatile flow blood pump for hemodialysis, urea is cleared from the blood approximately three times as fast as it is cleared in the prior art system utilizing a steady flow blood pump, while more desirable larger molecular weight blood constituents, such as vitamin $B_{12}$, are cleared from the blood less rapidly and therefore tend to be retained in the blood.

SUMMARY OF THE INVENTION

The invention is best summarized as a hemodialysis apparatus and method in which the customary steady flow blood pump is eliminated and replaced by a pulsatile flow blood pump which imparts to the system functional characteristics more closely resembling the human blood purification process involving the kidneys and heart.

The drawing FIGURE is a schematic view of a hemodialysis apparatus and method according to the present invention.

DETAILED DESCRIPTION

Referring to the drawings in detail wherein like numerals designate like parts, a hemodialysis system according to the present invention comprises a dialyzer 10, preferably a hollow fiber artificial kidney (HFAK). The dialyzer 10 includes dialysate and blood compartments 11 and 12 separated by a membrane 13. A dialysate reservoir 14 is provided and the conventional dialysate from this reservoir is pumped continuously through the compartment 11 by a steady flow dialysate pump 15, such as a Sarns 3500 Roller Pump or an equivalent steady flow pump.

The drawing FIGURE shows a patient's wrist and indicates cannulation of the radial artery 16 and a vein 17. Customarily, a surgeon creates an arterial-venous shunt above the wrist for this purpose.

Blood flows from the artery 16 to a pulsatile flow blood pump 18, in accordance with the essence of the invention. The pump 18 may be of the type disclosed in the above-referenced U.S. Pat. Nos. 4,143,425 and 4,293,961. The pulsatile flow pump 18 pumps blood into and through the compartment 12 of the dialyzer where the required purification of the blood takes place in a known manner. From the compartment 12, the purified blood is returned to the patient's vein 17 through a conduit 19 which includes a bubble trap 20. Except for the provision of the pulsatile flow blood pump 18, the hemodialysis system as shown in the drawing is conventional.

As explained previously, the improved system, in accordance with the present invention, clears low molecular weight urea from the blood approximately three times as fast as the urea is cleared in a prior art system having a steady flow pump. Larger molecular weight constituents, such as vitamin $B_{12}$, are also cleared somewhat more rapidly than when a steady flow blood pump is used, but less rapidly than the lower molecular weight products are cleared. This enables retention in the blood of some of the more desirable larger molecule constituents, such as vitamin $B_{12}$. The improved pulsatile flow hemodialysis apparatus and method resembles much more closely than the prior art nature's system of blood purification by the kidneys with the heart creating a pulsatile blood flow. The selective clearance of the lower weight noxious molecules, urea, and the heavier, more desirable molecules, vitamin $B_{12}$, realized by the improved system is thought to be a beneficial feature of the invention.

The results of a laboratory study of the phenomenon forming the basis of the invention can be summarized as follows.

Utilizing a Hollow Fiber Artificial Kidney (HFAK), the dialyzing properties of steady flow and physiologic pulsatile flow were compared in a laboratory setting. Steady flow was supplied by a Sarns 3500 Roller Pump and pulsatile flow by a University of Texas S 83 pulsatile flow pump, an externally valved, pre-load sensitive, displacement pump which produces physiologic wave form and stroke volume. Dialysate consisted of tap water and blood simulation consisted of physiologic saline solution containing a small molecular weight compound, urea, 2 mg/ml; a medium weight molecule, Nutra-Sweet ®, 2 mg/ml and a heavy molecule, vitamin $B_{12}$, 0.8 mg/ml. Flow rate with each pump was 200 ml/minute, pressures were physiologic and duration of dialysis was 120 minutes. Pumping rate of the pulsatile pump was 50 per minute. The results indicate a significantly more rapid clearance for all solutes with the pulsatile flow pump, the results being dramatic, fourfold, with the lighter molecules, urea.

The significant advantages of the invention over the prior art should be apparent to those skilled in the art.

It is to be understood that the form of the invention herewith shown and described is to be taken as a preferred example of the same, and that various changes in the shape, size and arrangement of parts may be resorted to, without departing from the spirit of the invention or scope of the subjoined claims.

We claim:

1. A pulsatile flow hemodialysis apparatus for purification of a patient's blood comprising a dialyzer having a dialysate compartment and a blood compartment, a membrane separating said compartments, a dialysate reservoir, a dialysate flow circuit communicating between said dialysate reservoir and said dialysate compartment, said dialysate flow circuit including means for providing a steady flow in the dialysate flow circuit comprising a steady flow dialysate pump for continuously pumping dialysate from the dialysate reservoir through said dialysate compartment, a blood flow circuit communicating between a dialyzer blood compartment and an artery and vein of a patient, said blood flow circuit comprising a single pump, said pump being a pulsatile flow blood pump, a first conduit having one end connected to the patient's artery, the opposite end of said first conduit communicating with the inlet of said pulsatile flow blood pump, the outlet of said pulsatile flow blood pump communicating with the inlet to said blood compartment to cause pulsatile flow therein on only one side of said membrane, a second conduit having one end connected to the outlet of said blood compartment, the opposite end of said second conduit being connected to the patient's vein, said pulsatile flow blood pump comprising an externally valved preload sensitive displacement pump producing a physiologic wave form and stroke volume for pumping blood from the patient's artery with sufficient force to drive the patient's blood through the blood compartment of the dialyzer in a physiologic manner and returning the blood to the vein of the patient, whereby hemodialysis is caused to closely simulate the patient's natural blood purification process performed by the patient's kidneys in conjunction with the pulsatile flow pumping action of the patient's heart, to thereby quickly clear urea from the patient's blood while more desirable larger molecular weight blood constituents tend to be retained longer in the blood.

* * * * *